(12) United States Patent
Roy et al.

(10) Patent No.: US 6,235,798 B1
(45) Date of Patent: May 22, 2001

(54) PROCESS FOR CONVERTING SYNTHESIS GAS IN THE PRESENCE OF A CATALYST BASED ON A GROUP VIII METAL, WHEREBY THE METAL PARTICLES ARE DISPERSED IN THE FORM OF AGGREGATES

(75) Inventors: Magalie Roy, Rueil Malmaison; Marie-Claire Marion, Villeurbanne, both of (FR)

(73) Assignees: Insitut Francais du Petrole, Rueil-Maimaison Cedex (FR); Agip S.p.A., Milan; Agip Petroli S.p.A., Roma, both of (IT)

( * ) Notice: Subject to any disclaimer, the term of this patent is extended or adjusted under 35 U.S.C. 154(b) by 0 days.

(21) Appl. No.: 09/398,460

(22) Filed: Sep. 17, 1999

(30) Foreign Application Priority Data

Sep. 18, 1998 (FR) .................................................. 98 11.723

(51) Int. Cl.[7] ............................ C07C 27/00; B01J 23/40

(52) U.S. Cl. .......................... 518/715; 518/700; 502/326
(58) Field of Search .................................. 518/700, 715; 502/326

(56) References Cited

U.S. PATENT DOCUMENTS 5,928,983 * 7/1999 Culross ................................ 502/170

FOREIGN PATENT DOCUMENTS 0 174 696   3/1986   (EP) .

* cited by examiner

*Primary Examiner*—Johann Richter
*Assistant Examiner*—J. Parsa
(74) *Attorney, Agent, or Firm*—Millen, White, Zelano & Branigan, P.C.

(57) ABSTRACT

The invention relates to a hydrocarbon synthesis process in the presence of a catalyst that comprises a substrate, at least one metal of group VIII that comprises metal particles, preferably cobalt, characterized in that the group VIII metal particles of the catalyst are deposited on the substrate in the form of aggregates.

23 Claims, 3 Drawing Sheets

PROCESS FOR CONVERTING SYNTHESIS GAS IN THE PRESENCE OF A CATALYST BASED ON A GROUP VIII METAL, WHEREBY THE METAL PARTICLES ARE DISPERSED IN THE FORM OF AGGREGATES

This invention relates to the use of a catalyst that comprises at least one substrate, at least one metal of group VIII in the form of metal particles, in a process for synthesis of hydrocarbons from a mixture that comprises CO—($CO_2$)—$H_2$ (i.e., a mixture that comprises CO—$H_2$ that optionally comprises $CO_2$, called synthesis gas), more particularly the use that makes it possible to carry out the conversion of synthesis gas into a mixture of saturated linear hydrocarbons that essentially consist of C5' hydrocarbons (i.e., that have at least 5 carbon atoms per molecule) or more specifically into a mixture of essentially linear and saturated hydrocarbons that contain at least 25% by weight of C5' hydrocarbons relative to all of the hydrocarbons that are formed. The invention also relates to the catalyst that is used as well as its preparation process.

It is known to one skilled in the art that the synthesis gas can be converted into hydrocarbons in the presence of catalyst that contains transition metals. This conversion that is operated at high temperature and under pressure is known in the literature under the name of Fiecher-Tropsch synthesis. Metals of group VIII of the periodic table, such as iron, ruthenium, cobalt and nickel thus catalyze the transformation of CO—($CO_2$)—$H_2$ mixtures (i.e., a CO—$H_2$. mixture that optionally comprises $CO_2$, called synthesis gas) into liquid and/or gaseous hydrocarbons.

The products that are prepared by Fischer-Tropsch synthesis in the presence of catalysts that comprise metals of group VIII have a very wide distribution in terms of molecular weight.

Thus, only a small proportion of products that are obtained are located in the range of the middle distillates that consist of kerosene and gas oil fractions, whereby the kerosene fraction or fractions consist(s) of a hydrocarbon mixture whose boiling points are between 140° C. and 300° C., and whereby the gas oil fraction or fractions consist(s) of a hydrocarbon mixture with boiling points of between 180° C. and 370° C. during an atmospheric distillation as carried out on a crude by one skilled in the art.

Significant efforts have been undertaken since 1973 to improve the yield of middle distillates that are based on the conversion of the synthesis gas.

Various methods have been described and developed in the prior art that are intended to improve the distribution of metal to limit the diffusional phenomena inside the grain. The substrate is then coated or covered so that the metal remains on the periphery of the grain.

Patent Application EP 0174696 A describes a process for preparation of a Fischer-Tropach catalyst with a cobalt base, where the cobalt is distributed in such a way that $\Sigma Vp/\Sigma Vc$ <0.86 (whereby $\Sigma Vp$ is the quantity of Co that is contained in the periphery of the solid, and whereby $\Sigma Vc$ is the quantity of Co that is contained in the entire solid). The inventor shows that this distribution promotes the formation of C5$^+$. The catalyst is prepared by impregnation of the substrate (preferably silica) that is already immersed in water for 30 seconds and can contain a promoter, preferably zirconium.

U.S Pat. No. 5,036,032 describes the preparation of a catalyst with a cobalt base that makes it possible to increase the dispersion of cobalt over the outside surface of the substrate. The preparation method makes it possible to increase the density of surface active sites by using a precursor of sufficient viscosity to prevent penetration in the pores by capillary action. The direct reduction without a calcination stage makes it possible to increase the dispersion. $SiO_2$ is preferred as a substrate. The diffusional limitations are thus avoided.

U.S. Pat. No. 4,977,126 also describes a surface dispersion method by vaporization of a liquid in which the metal compound is dissolved. A peripheral layer thus is formed.

Other U.S. Pat. No. 4,605,679, U.S. Pat. No. 4,729,981, EP 0 535 790 A describe modifications of the reduction stage/activation.

Finally, Patent Application EP 0 736 326 A describes a new method for preparation of the catalyst with cobalt that comprises an impregnation stage that is followed by a drying stage of the catalyst under a pressure that is less than the atmospheric pressure.

The influence of the size of the particles on the activity of the catalyst was widely discussed in the literature. In the case of the transformation of synthesis gas into liquid and/or gaseous hydrocarbons, it was shown that the specific activity was independent of the dispersion of the metal and the nature of the substrate [E. Iglesia, Applied Catalysis A: General 161 (1997) 59].

The specific activity corresponds to the activity of the catalyst that is brought back to the number of metal atoms that are accessible to the number of molecules to be transformed. The number of accessible metal atoms can be determined by techniques for chemisorption of sampler molecules (oxygen, hydrogen, carbon monoxide) or from the size of the particles that is determined by electronic microscopy. Theme different techniques are well known to one skilled in the art.

This invention relates to a process for synthesis of hydrocarbons from a mixture that comprises carbon monoxide and CO—$H_2$ hydrogen, optionally carbon dioxide $CO_2$, in the presence of a catalyst that comprises a substrate and particles of at least one metal of group VIII of the periodic table of elements that is (are) deposited on the substrate, characterized in that at least a portion of the particles of the metal of group VIII of the catalyst are not isolated relative to one another.

The applicant discovered, surprisingly enough, that when at least a portion of the metal particles is not isolated relative to the other particles that are deposited on the substrate but that the particles form agglomerates or aggregates, the catalyst has a selectivity of C5$^+$ that is improved relative to a catalyst that has isolated particles. The particles of the catalyst according to the invention are generally between 50 and 500 Å in size, preferably between 60 and 400 Å. The catalyst according to the invention has a selectivity of C5$^+$ that is improved relative to a catalyst that comprises isolated particles that are between 50 and 500 Å in size and relative to a catalyst that has isolated particles that are greater than 500 Å in size. These particles can be dispersed on the periphery or inside the pores of the substrate or at the same time on the periphery and inside the pores.

The aggregation state between metal particles is defined by the existence of at least one contact zone between at least two particles. The aggregation state is characterized by an analysis by microscopy with transmission of the catalyst before or after reduction of the active phase.

For the catalyst according to the invention, analysis by microscopy shows that at least 60% of the particles, preferably 80% of the particles, and even more preferably 90% of the particles have at least one contact zone with at least one other particle, and preferably with at least two other particles. The particles are preferably deposited in the form of essentially spherical agglomerates that are between 500 and 100,000 Å in size. They can also be used in the form of clusters or streams or any other configuration to have at least one contact zone with at least one other particle, preferably with two other particles This invention involves a catalyst that is used in Fischer-Tropsch synthesis whose performances are particularly stable and which after reduction under hydrogen results in the conversion of the synthesis gas into a linear and saturated hydrocarbon mixture that contains at least 50% by weight of $C_5^+$ hydrocarbons and at least 20% of methane relative to all. of the hydrocarbons that are formed.

The conditions of use of said catalysts for the synthesis of hydrocarbons are usually as follows:

The catalyst that comprises at least one metal of group VIII that is impregnated on a substrate is dried and then calcined. The catalyst is then pre-reduced by at least one reducing compound, for example selected from the group that is formed by hydrogen, carbon monoxide and formic acid, optionally brought into contact with an inert gas (nitrogen, for example, in a molar ratio of reducing compound/(reducing compound+inert gas) of between 0.001:1 to 1:1.

The reduction is carried out in an aqueous phase between 100° C. and 600° C., preferably between 150° C. and 400° C., between 0.1 and 10 MPa and at an hourly volumetric flow rate of between 100 and 40,000 volumes of mixture per volume of catalyst and per hour. This reduction can also be carried out in a liquid phase, whereby the catalyst is suspended in an inert solvent, for example a paraffinic fraction that comprises at least one hydrocarbon that has at least 5, preferably at least 10 carbon atoms per molecule if later the hydrocarbon synthesis reaction takes place in a liquid phase that comprises at least one hydrocarbon that has at least 5, preferably at least 10 carbon atoms per molecule.

The conversion of the synthesis gas into hydrocarbons is then operated under a total pressure that is usually between 0.1 and 15 Mpa and preferably between 1 and 10 MPa, whereby the temperature is generally between 150 and 350° C. and preferably between 170 and 300° C.

The hourly volumetric flow rate is usually between 100 and 20,000 volumes of synthesis gas per volume of catalyst and per hour and preferably between 400 and 5,000 volumes of synthesis gas per volume of catalyst and per hour, and the H2/CO ratio in the synthesis gas is usually between 1:2 and 5:1, and preferably between 1.2:1 and 2.5:1.

The catalyst is generally used in calibrated fine powder (about 10–700 microns) or in particles with an equivalent diameter of between about 2 and 10 mm, respectively in the presence of a liquid phase (under the operating conditions) or a gaseous phase. The liquid phase can consist of at least one hydrocarbon that has at least, preferably at least 10, carbon atoms per molecule.

The element of group VIII of the periodic table is selected from among iron, cobalt and ruthenium. The metal of group VIII is preferably cobalt.

The substrate of the catalyst according to the invention comprises at least one refractory oxide that is generally selected from among the magnesium oxides, aluminum oxides, silicon oxides or zirconium oxides, by themselves or mixed with one another or with oxides of other elements of the periodic table. The substrate that is used will preferably be alumina.

Carbon, alumino-silicates, clays or any other compound that can be used as a substrate can also be used. This substrate can be used in powder form or after shaping; any shaping technique is suitable to the invention.

The introduction of the metal of group VIII is done generally to obtain particles of between 50 and 500 Å in size that are dispersed over a substrate such that at least 60% of the particles, preferably at least 80% of the particles and even more preferably at least 90% of the particles have at least one contact zone with at least one other particle and preferably with at least two other particles.

A technique for preparing the catalyst that is particularly suitable is the imoreanation of a solution that contains metal oxide particles and/or metal particles that are to be deposited in suspension. The solvent may be an aqueous solvent, for example water, or an organic solvent.

To increase the contact zones between the particles, the solution can contain a limited concentration of complexing agent that makes it possible to stabilize it, whereby the completing agent is not essential, however, Another technique for preparing the catalyst consists in impregnating with an aqueous solution a precursor of the metal of group VIII of the periodic table, for example an aqueous solution of salts such as cobalt nitrate and cobalt acetate. The aqueous solution can be heated to a temperature of between ambient temperature and 120° C., before impregnation.

The impregnation can be done drop by drop on the substrate that is itself heated to a temperature of between ambient temperature and 200° C., thus inducing the evaporation of the aqueous solution from the time of contact with the substrate.

After the solutions are deposited by impregnation, the catalyst is generally dried under an air or nitrogen flow at a temperature of between 80° C. and 120° C., optionally calcined under an air or nitrogen flow at temperatures of between 120° C. and 500° C. and reduced to temperatures that are between 100° C. and 500° C.

The content by weight relative to the total weight of metal catalyst of group VIII is generally between 0.1 and 50%, preferably between 1 and 30%.

The catalyst can also contain other additional elements such as, for example, at least one alkaline metal, promoters such as, for example, at least one element that is selected from among ruthenium, molybdenum and tantalum. The content by weight of an additional element relative to the total weight of catalyst is generally between 0.01 and 5%. These additional elements can be introduced at the same time as the metal of group VIII or in at least one subsequent stage.

In a particular embodiment of the invention, the catalyst contains cobalt and ruthenium.

In another particular embodiment of the invention, the catalyst contains cobalt and tantalum.

BRIEF DESCRIPTION OF THE DRAWINGS

To illustrate the invention, a set of photomicrographs that are representative of catalysts according to the invention is provided as an attachment.

Figure 1:
FIGS. 1 and 2 show aggregates of particles of varied shape.
Figure 2:
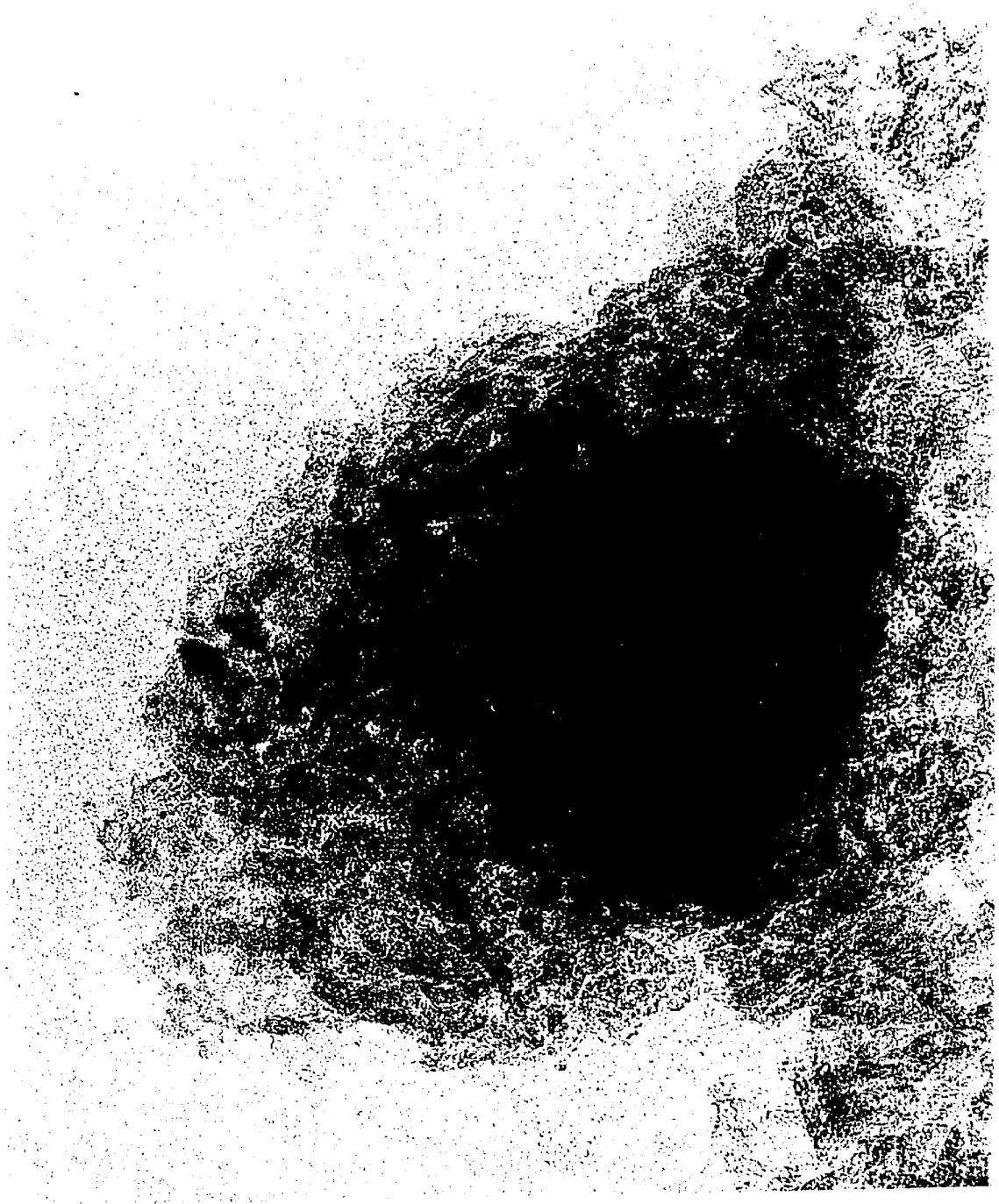
Figure 3:
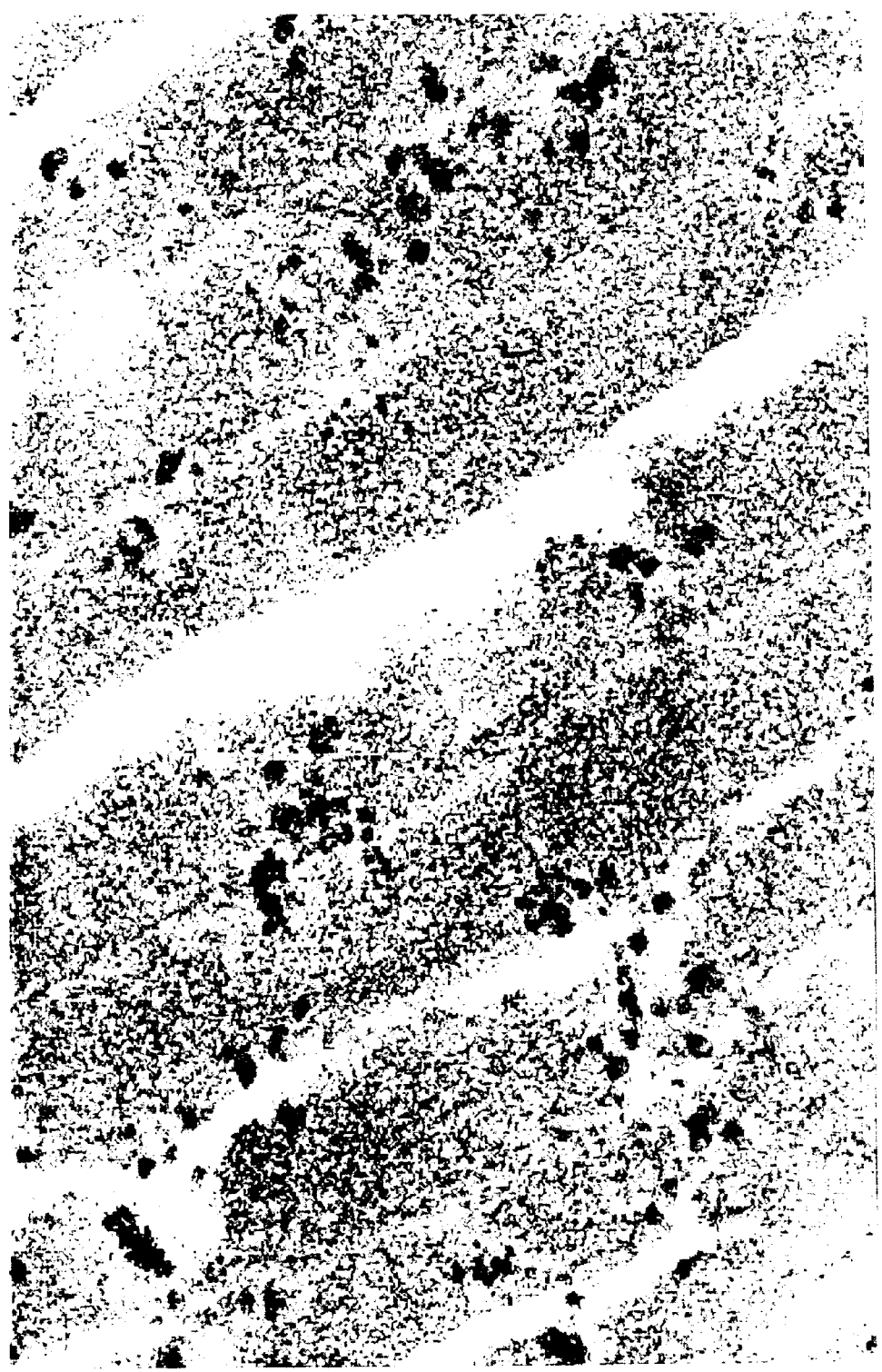
FIG. 3 is given as a comparison and shows isolated particles.

The following examples illustrate the invention.

EXAMPLE 1

According to the Invention

Catalyst A

A catalyst A, Co/Al2O3, is prepared by impregnation of an alumina powder with a specific surface areas 180 m²/. This substrate comes in powder form with a grain size of between 10 and 150 microns.

This substrate is heated to 100° C. on a rotating holding plate and at the same time is impregnated by an aqueous solution of cobalt nitrate.

After impregnation, the substrate is calcined at 400° C.

The final cobalt content is 12.5%.

The cobalt particles have a size of between about 150 and 180 Å.

Analysis by microscopy with transmission of this catalyst shows that 98% of the cobalt particles form spherical aggregates that are between 300 and 4,000 Å in size.

EXAMPLE 2

Comparative

Catalyst B

A catalyst B is prepared from the substrate that is described in Example A.

This substrate is impregnated by an aqueous solution of cobalt nitrate at ambient temperature. After impregnation, the substrate is dried at 120° C. and calcined at 400° C.

The final cobalt content is 13%.

Microscopic analysis shows the presence of cobalt particles that are greater than 500 Å in size at 100%, isolated, and other particles that are between 150 and 300 Å in size, isolated.

EXAMPLE 3

Comparative

Catalyst C

A catalyst C, $Co/SiO_2$, is prepared by the sol-gel method that is described in U.S. Pat. No. 5,302,622.

The specific surface area is 250 m2/g.

the cobalt content is 25%.

The cobalt particles are between 130 and 200 Å in size with some particles that are greater than 580 Å in size.

45% of the cobalt particles are isolated.

EXAMPLE 4

According to the Invention

Catalyst D

A catalyst D is prepared from the substrate that is described in Example A.

The cobalt is impregnated in a first stage from a cobalt nitrate solution. The solid is then left to cure at ambient temperature for 12 hours.

The solid is then dried at 120° C. and calcined at 400° C. The ruthenium is then impregnated in aqueous solution. The solid is dried at 110° C. and calcined at 300° C.

The cobalt content is 15%, and the ruthenium content is 0.25%.

99% of the cobalt particles that are obtained are between 150 and 300 Å in size and form agglomerates.

EXAMPLE 5

Comparative

Catalyst E

A catalyst E is prepared from the substrate that is described in Example A.

The cobalt is impregnated in a first stage from a cobalt nitrate solution. The solid is then dried at 120° C. and calcined at 400° C. then reduced in a tubular reactor under pure hydrogen at 400° C. and passivated under oxygen.

The ruthenium is then impregnated in aqueous solution. The solid is dried at 110° C., calcined at 300° C. and again reduced in a tubular reactor under pure hydrogen at 400° C. and passivated under oxygen.

The cobalt content is 15%, and the ruthenium content is 0.25%.

The cobalt particles that are obtained have small sizes of between 50 and 100 Å, and 42% of the particles are isolated.

EXAMPLE 6

Catalytic Tests

Catalysts A, B. C, D and E, whose preparations are described in Examples 1 to 5 above, are tested in a gaseous phase in a fixed bed unit that operates continuously on 20 cm³ of catalyst.

The catalysts are first reduced in situ at 350° C. for 12 hours under a mixture of hydrogen and nitrogen that contains 30% hydrogen, then for 12 hours under pure hydrogen.

The test conditions of the catalysts are as follows:

T°C.=220° C.,

Pressure=2 MPa

Hourly volumetric flow rate (VVH)=1500 h$^{-1}$ $H_2/CO$ molar ratio=2/1

TABLE

Conversion at Synthesis Gas into Hydrocarbons

| Catalyst | % of isolated particles | Composition | Conv of CO (% of vol after 100 hours) | Distribution of formed products (% by weight) | | |
|---|---|---|---|---|---|---|
| | | | | C1 | C1–C4 | C5+ |
| A (invention) | 2% | Co | 55 | 12.5 | 25.2 | 74.8 |
| B (Comparative) | — | Co | 70 | 21 | 35.5 | 64.5 |
| C (Comparative) | 45% | Co | 68 | 33 | 45 | 55 |
| D (invention) | 1% | Co-Ru | 65 | 11 | 22.5 | 77.5 |
| E (Comparative) | 42% | Co-Ru | 45 | 26.5 | 41.5 | 58.5 |

The results of the table show that the process according to the invention in the presence of a catalyst, in which the major part of the metal particles are not isolated but in an aggregated form, presents an improved C5+ selectivity relative to the catalysts of the prior art.

What is claimed is:

1. In a process for synthesis of hydrocarbons, comprising reacting a mixture comprising carbon monoxide and hydrogen in the presence of a catalyst comprising a substrate, particles of at least one metal of group VIII of the periodic table deposited on the substrate, the improvement wherein the catalyst has a degree of particle contact such that at least 60% of the particles of said metal of group VIII of the catalyst have at least one contact zone with at least one other particle.

2. A process according to claim 1, wherein at least a portion of the metal particles of the catalyst have at least one contact zone with at least two other particles.

3. A process according to claim 1, wherein at least 80% of the metal particles of the catalyst have at least one contact zone with at least one other particle.

4. A process according to claim 1, wherein the metal of group VIII comprises cobalt.

5. A process according to claim 1, wherein the catalyst further contains ruthenium.

6. A process according to claim 1, conducted at a total pressure between 0.1 and 15 MPa, a temperature between 150 and 350° C., with an hourly volumetric flow rate of between 100 and 20,000 volumes of synthesis gas per volume of catalyst per hour, and with an $H_2/CO$ ratio in the synthesis gas of between 1:2 and 5:1.

7. A process according to claim 6, wherein the $H_2/CO$ ratio is between 1.2:1 and 2.5:1.

8. A process according to claim 4, wherein the catalyst further contains ruthenium.

9. A process according to claim 2, wherein metal of group VIII comprises cobalt.

10. A process according to claim 3, wherein metal of group VIII comprises cobalt.

11. A process according to claim 10, wherein the catalyst further contains ruthenium.

12. A process according to claim 1, wherein the metal particles of group VIII have a particle size between 50 and 500 Å.

13. A process according to claim 1, wherein the catalyst has a selectivity towards $C5^+$ hydrocarbon which is higher than a similar catalyst having isolated particles.

14. A process according to claim 3, wherein at least a portion of the metal particles of the catalyst have at least one contact zone with at least two other particles.

15. A process according to claim 3, wherein the catalyst has a particle size between 50 and 500 Å.

16. A process according to claim 1, wherein at least 90% of the metal particles of the catalyst have at least one contact zone with at least one other particle.

17. A process according to claim 16, wherein at least a portion of the metal particles of the catalyst have at least one contact zone with at least two other particles.

18. A process according to claim 17, wherein the catalyst has a particle size between 50 and 500 Å.

19. A process according to claim 1 are in the form of essentially spherical agglomerates having a size between 500 and 100,000 angstroms.

20. A process according to claim 16, wherein metal of group VIII comprises cobalt.

21. A process according to claim 18, wherein metal of group VIII comprises cobalt.

22. A process according to claim 1, wherein the metal particles of group VIII have a particle size of between 60 and 400 angstroms.

23. A process according to claim 1, further comprising determining said degree of particle contact of said catalyst prior to the synthesis reaction.

* * * * *